United States Patent [19]

Kavoussi

[11] Patent Number: 5,103,840
[45] Date of Patent: Apr. 14, 1992

[54] VISCOELASTIC COLLAGEN GEL FOR OPHTHALMIC SURGERY

[76] Inventor: Harold P. Kavoussi, 2717 N. San Angelo Dr., Claremont, Calif. 91711

[21] Appl. No.: 519,739

[22] Filed: May 7, 1990

[51] Int. Cl.$^5$ .............................................. A61F 2/14
[52] U.S. Cl. ............................. 128/899; 128/DIG. 8
[58] Field of Search ....................... 128/DIG. 8, 899; 530/356, 399; 514/25, 4, 57

[56] References Cited

U.S. PATENT DOCUMENTS

| | | |
|---|---|---|
| 3,949,073 | 4/1976 | Daniels et al. . |
| 4,141,973 | 2/1979 | Balazs . |
| 4,164,559 | 8/1979 | Miyata et al. . |
| 4,233,360 | 11/1980 | Luck et al. ............... 128/DIG. 8 X |
| 4,260,228 | 4/1981 | Miyata . |
| 4,264,155 | 4/1981 | Miyata . |
| 4,264,493 | 4/1981 | Battista . |
| 4,328,803 | 5/1982 | Pape . |
| 4,382,081 | 5/1983 | Sundeen et al. . |
| 4,404,033 | 9/1983 | Steffan . |
| 4,409,332 | 10/1983 | Jeffries et al. . |
| 4,424,208 | 1/1984 | Wallace et al. . |
| 4,532,267 | 7/1985 | Allan . |
| 4,540,568 | 9/1985 | Trager et al. . |
| 4,559,304 | 12/1985 | Kasai et al. . |
| 4,713,375 | 12/1987 | Lindstrom et al. ................... 514/57 |
| 4,713,446 | 12/1987 | Devore et al. ............ 128/DIG. 8 X |
| 4,851,513 | 7/1989 | Devore et al. ............ 128/DIG. 8 X |
| 5,013,714 | 5/1991 | Lindstrom et al. ..................... 514/4 |

Primary Examiner—Robert A. Hafer
Assistant Examiner—Sam Rimell

[57] ABSTRACT

The present invention embodies a composition particularly adapted for use as an ophthalmic viscosurgical material for use in the anterior chamber, posterior chamber and vitreous cavity of the eye consisting essentially of a mixture of purified collagen Type II and Type IV, which is the basic composition of naturally occuring vitreous in the eye. The invention further embodies an improved ophthalmic viscosurgical procedure wherein the anterior chamber of the eye is filled with a space - filling corneal endothelium and ocular tissue protective surgical material, the improvement comprising the utilization of an ophthalmic surgical material having the above described composition. Specifically, the collagen gel of this invention is useful in the following procedures: (a) as an anterior segment implant to maintain anterior chamber depth and to protect the corneal endothelium during intracapsular and extracapsular cataract len extraction and phacoemulsification and during intraocular lens implantation; (b) as a surgical adjunct during corneal transplant surgery to protect the corneal endothelium from contacting other ocular tissues and to prevent post - operative graft dislocation; (c) as a posterior segment implant during intraocular lens implantation and as an adjunct to retinal detachment surgery; and (d) as a vitreous replacement.

1 Claim, No Drawings

VISCOELASTIC COLLAGEN GEL FOR OPHTHALMIC SURGERY

BACKGROUND

1. Field of the Invention

The present invention relates to novel viscoelastic viscosurgical materials and ophthalmic surgical techniques utilizing the materials.

2. Prior Art

In ophthalmic surgical procedures such as intraocular lens implantation, cataract surgery, retinal detachment repair, etc., there exists a need for viscous, gel-like compositions to fill the chambers of the eye to protect sensitive tissue such as the corneal endothelium from trauma, see U.S. Pat. No. 4,141,975; Pruett et al, Arch. Ophthalmol., 97:2325 (1979); Holmberg et al, Ophthalmology, 91:45 and 53 (1984); Pope et al, ophthalmology, 87:669 (1980): Mac Rae et al, Am. J. Ophthalmol, 13:811 (1981).

The most commonly employed materials are solutions of hyaluronic acid (HA), chondroitin sulfate (CS) and methylcellulose (MS). HA has been the most widely used and appears to owe its unusual rheological and viscoelastic solution properties to its polyanion polyelectrolyte molecular structure.

However, HA is extremely expensive. Furthermore, it requires extraordinary purification to remove as much proteinaceous immunogenic material as possible but still may provoke immune reactions in some patients. Its use is also often accompanied by significant undesireable intraocular pressure rise which necessitates washing HA for the eye at the end of surgery and may also require antiglaucoma therapy.

Chondroitin sulfate solutions do not inhibit pseudoplastic behavior, i.e., the viscosity is relatively constant at all shear rates. Accordingly chondroitin sulfate solutions do not exhibit the same degree of anterior chamber support as pseudoplastic fluids such as those prepared using sodium hyaluronate. Furthermore, since the viscosity of the chondroitin sulfate solutions does not decrease at increasing shear rates (as do pseudoplastic materials) extremely high pressures are needed to apply or irrigate chondroitin sulfate solutions through a syringe (Mac Rae et al; "The Effects Sodium Hyaluronate, Chondroitin Sulfate, and Methyl Cellulose on the Corneal Endothelium and Intraocular Pressure, Am. J. of Ophthalmology, 95:332–341 (1983). Additionally, Commercially available chondroitin sulfate solutions (20 to 50 percent solutions) have osmolarities in excess of 500 mOsm. Such high osmolarities are detrimental to the corneal endothelium. Lastly, as reported by Mac Rae et al, in the *American Journal of Ophthalmology*, supra, 20 percent chondroitin sulfate may cause a sharp increase in intraocular pressure in the first one to four hours after intracameral injection and, thererfore, anterior chamber washout is indicated.

It is an object of the present invention to provide improved ophthalmic viscoelastic surgical materials and ophthalmic surgical thecniques embodying same which are not subject to the above-noted disadvantages.

SUMMARY OF THE INVENTION

The present invention embodies a composition particularly adapted for use as an ophthalmic viscosurgical material for use in the anterior chamber, posterior chamber, and vitreous cavity of the eye, consisting essentially of a mixture of purified collagen Type II and Type IV having molecular weights of 285,000 and 532,000 respectively.

The invention further embodies an improved ophthalmic viscosurgical procedure wherein the anterior chamber of the eye is filled with a space-filling corneal endothelium and ocular tissue protective surgical material, the improvement comprising the utilization of an ophthalmic surgical material having the above described composition.

Additionally, native collagen is available from a wide variety of sources, e.g. human placenta, bone, tendon, hide, etc. accordingly, collagen is more abundant and less expensive to obtain than tissue derived hyaluronic acid.

DETAILED DESCRIPTION OF THE INVENTION

The below-listed terms are employed throughout the specifications and claims and they are defined as follows:

(1) "Viscoelastic" material refers to certain viscous solutions or compositions having the requisite viscous gel-like properties which enable their use to fill the anterior chamber of the eye.

(2) "Viscosurgical" material or technique refers to the viscoeleastic surgical materials inserted in the eye or the surgical techniques employed to fill the anterior chamber of the eye during cataract, lens implant, etc., surgeries.

(3) "Collvisc" as used herein refers to the purified combination of Type II ands Type IV collagen.

(4) "Physiologically acceptable" is employed to refer to materials which, when in contact with tissues in the body, are not harmful thereto. The term is intended in this context to define aqueous solutions which are approximately isomolar with the physiological environment of the eye. Generally such media have an osmolarity of the order fo 250–300 and are buffered to maintin a PH of from about 7.0 to 7.5. The process by which collvisc is prepared is as follows:

COLLECTION OF COLLAGEN SOURCE MATERIAL

The method of obtaining the collagen from the crude collagen source e.g., tendon, hide, bovine, nasal septa, human placenta, etc., is normally not critical, and some flexibility may be used in the selection of the particular tissue and the method applied thereto. Applicant prefers to extract purified collagen Type II from bovine nasal septa and purified collagen Type IV from human placenta. Type II collagen was extracted and purified from bovine nasal septa, the tissue was first stirred in ice-cold 4 m guanidine HCL/50 mM sodium acetate PH 5.8 for 2 h. This was followed by a limited pepsin digestion. This was followed by purification by precipitation from acidic solution, neutral solution, a low ionic strength precipitation and finally by differential salt precipitation from neutral solution.

Type IV collagen was extracted and purified from human placenta. The tissue was extracted and purified at 4 C. in the presence of 10 mM $Na_2$ EDTA, 10 mM N-Ethylmaleimide, 1 mg/ml leupeptin, 1 mM benzamidine-HCL. In addition, the initial washing and homogenization steps contained 0.1M alpha-aminocaproic acid. The tissue was homogenized in 3.4M Na Cl, 50 mM Tris-HCL at PH 7.4 followed by sequential extractions with: 0.5M Na Cl, 50 mM Tris-HCL, PH 7.4; 2.0M guanidine-HCL, 50 mM Tris-HCL PH 7.4 and finally 2.0M guanidine-HCL, 50 mM Tris-HCL PH 7.4 with 2 mM dithiothreitol (DTT). The final extract containing the Type IV collagen is brought to 3.5M Na Cl to precipitate the Type IV collagen. Once purified collagen Type II and purified collagen Type IV are extracted and purified they are mixed together in varying proportions to form the viscoelastic collagen compound, "collvisc". Collvisc can be made less viscous (solution form) or more viscous (gel form) depending on the proportions of the mixture of purified collagen Type II and purified collagen Type IV. The experimentally observed values of molecular weight, translational diffusion coefficient, particle scattering factor at 175.5° and a wavelength of 633 nm and intrinsic viscosity at 22° C. for collagen Type IV were 532,000, $0.66 \times 10^{-7}$ cm$^2$ s$^{-1}$, 0.492 and 74.7 ml/g respectively. The experimentally observed values of molecular weight, translational diffusion coefficient, particle scattering factor at 175.5° and a wavelength of 633 nm for collagen Type II were 285,000, $0.845 \times 10^{-7}$ cm$^2$ s$^{-1}$, and 0.450, respectively.

TRANSPARENCY

Collvisc for ocular use is transparent, colorless, and has refractive indices approximately equal to the aqueous humor make it particularly appropriate as aqueous or vitreous replacements during intracapsular, extracapsular and phacoemulsification cataract extraction, intraocular lens implantation, corneal transplantation, and repair of retinal detachment. Transparency assures the surgeon that he/she can manipulate freely and maintain full control of the surgical procedure with complete and clear visibility in the presence of any quantity of the vicoelastic collagen gel.

VISCOELASTICITY

Collvisc exhibits what is known as the Weissenberg Effect, indicating that it is viscoelastic. The Weissenberg Effect describes the tendency in viscoelastic solutions for flow to occur at right angles to an applied force. When a rotating rod is lowered into a Newtonian (nonviscoelastic) liquid, the liquid is set into rotation and tends to move outwards, leaving a depression around the rod. When the rotating rod is lowered into a viscoelastic liquid, the liquid may acutally climb up the rod. The rotation of the rod causes the liquid to be sheared circularly and, because of its elastic nature, it acts like a stretched rubber band tending to squeeze liquid in towards the center of the vessel and, therefore, up the rod. Collvisc due to its viscoelastic character has lubricative properties which make it particularly useful as a protective coating on instruments and implants which are used near sensitive cellular and tissue surfaces. When used in the anterior chamber, collvisc maintains anterior chamber depth and protects the corneal endothelium during intracapsular, extracapsular, and phacoemulsification cataract lens extraction and during intraocular lens implantation. Viscoelasticity is also important in vitreous surgery, in order that the collagen gel be able to push back the retina to its normal position and not flow through the hole behind the retina. Furthermore, viscoelastic gels, provide long lasting support to the retina until it is healed, and maintain the rheological properties of the vitreous.

PSEUDOPLASTICITY

For ophthalmic applications a pseudoplastic material is ideal. At high shear stresses, i.e., during surgery when the eye tissues, instruments and/or implants are being manipulated within the eye, the viscosity of the material decreases thereby reducing the drag force on adjacent tissues, while at low shear stresses when the material is at rest the viscosity is high and the material acts as an effective lubricant for implants and/or for tissue surfaces which move relative to each other.

Additionally, pseudoplasticity permits the surgeon to move the collagen gel with relative ease through small bore needles and into small tissue spaces.

THIXOTROPY

A thixotropic liquid may be defined as a pseudoplastic material which is able to regain its viscosity when allowed to rest for an extended period of time after being stressed. Collvisc is able to regain its steady state viscosity after being injected through a syringe.

OSMOLARITY

Collvisc has particular applicability in ophthalmic surgery as an aqueous or vitreous replacement. The aqueous humor may be replaced by collvisc after various intraocular or extraocular surgical procedures in order to prevent cellular invasion of the anterior chamber, which would endanger the regeneration and function of the iris, ciliary body and corneal endothelium. Collvisc may also be used as a biological prosthesis in the anterior chamber after cataract surgery in order to push back prolapsed vitreous and, to provide separation between the vitreous and cornea. Further, collvisc can be used in the anterior chamber after keratoplasty to prevent adhesion formation between the corneal wound and the iris.

Collvisc may be implanted into the vitreous cavity after extensive intavitreal surgery (removal of hemorrhages, opacities, etc.,) to prevent excessive cellular reaction, and development of fibrous bands and preretinal tissue membranes.

Furthermore, collvisc is useful in retinal detachment surgery to provide a viscoelastic tool in the manipulation necessary for reattachment of the retina, to facilitate the intraocular wound healing by preventing excessive fibrous tissue formation and development of intravitreal scar tissue.

Collvisc adheres to hydrophobic polymeric surfaces such as polymethylmethacrylate or polyporpylene intraocular lenses. Thus, intraocular lenses can easily be coated with collvisc thereby causing less trauma and hazard during insertion into the anterior or posterior chambers of the eye. Collvisc can also be used as a wetting agent in contact lens solutions. Such wetting solution would remain on the lens for a longer time than previously known wetting solutions, thereby prolonging the comfort afforded the lens wearer.

Collvisc can have use as a vehicle for medication in ophthalmic or orthopedic applications to prolong the effect of the drug.

Collvisc is useful in other therapeutic applications to prevent fibrous tissue formation and the consequent development of adhesion and scars. For example, in cases of traumatic arthritis, osteoarthritis and bursitis it is contemplated that collvisc can be used to replace the synovial fluid in a synovial space to impede the development of intra-articular fibrous tissue (pannus, ankylosis, adhesions) and to support the healing process of cartilage and synovial tissue. As used herein, the term "synovial space" is intended to mean that space which separates joints, tendons and/or bursae.

In arthroplasty, osteotomy and all types of intra-articular surgery, such as arthoscopy, collvisc can be used to protect the articular cartilage surfaces from postoperative injury and from the possible harmful effect of prosthetic surfaces, to prevent excess fibrous tissue formation and to promote the normal healing of the soft tissues and cartilage.

It is further contemplated that collvisc can be implanted between tendons and their sheaths to minimize adhesion formation after any surgical procedure or around peripheral nerves and nerve roots after injury or surgery when damage to the connective tissue around the nerve is extensive and excessive scar formation is expected. Implantation of collvisc around the healing (regenerating) nerve may protect it from invasion by connective tissue cells.

In order to prevent adhesion formation between two endothelial or connective tissue membranes, collvisc can be implanted between mesothelial, pericardial and pleural sheets.

Collvisc can be used to separate tissue surfaces. The viscoelastic properties of collvisc would protect the tissue during surgical manipulation and postoperatively. Collvisc would be beneficial in improving the gliding function of muscle sheaths and tendon sheaths in traumatic injuries.

In orthopedic or cardiovascular surgery collvisc would be useful to lubricate and coat implants, further it could be used to prevent vascular grafts from contacting body fluids, and could also be used as a component of synthetic vessles. Furthermore, collvisc would be useful as moisturizers and lubricants in cosmetic creams and lotion.

Other uses for collvisc will undoubtedly occur to those skilled in the art and thus, the foregoing description does not limit the possible applications.

In order more clearly to disclose the nature of the present invention, the following examples will now be described. It should be understood, however, that this is done solely by way of example and is intended neither to delineate the scope of the invention nor limit the ambit of the appended claims. Biocompatibility studies in rabbits were conducted as follows.

EXAMPLE 1

Healthy NZW rabbits (2.5-3.5 kg) were selected for the study. All rabbits were subjected to a biomicroscopic slit lamp exam (SLE) prior to surgery. Only those with no anterior segment abnormalities were used. They were followed for one week after anterior chamber (A.C.) injection. Each rabbit was individually housed with cage identity cards for identification purposes. The rabbits were given standard food and water adlibitum during the course of study.

The test material was injected in the A.C. of rabbit eyes to evaluate post-operative biocompatibility of the test material in direct contact with living ocular tissues. Placement in the A.C. facilitates microscopic (SLE) evaluation of any tissue reactions as well as direct viewing of the viscoelastic material throughout the period of the study.

Controls consisted of a similar procedure using BSS (Alcon) in the opposite eye of the same rabbit. Each animal was weighed and sexed prior to surgery.

The surgical procedure described below was followed:

1. General anesthesia was induced by 20 mg/kg Ketamine Hydrochloride (Ketaset, 100 mg/ml, Bristol U.S.A.) and 4 mg/kg xylazine (Rompun, 20 mg/ml Haver-Lockhart, U.S.A.) injected I.M.
2. SLE exam of the anterior segment.
3. Tetracaine (0.5% eye drops) applied to the eye to anesthetize the cornea.
4. Inserted a wire speculum.
5. Penetrated into the A.C. with a 25 g or smaller needle at the cornea-limbal junction.
6. Aspirated 0.1–0.2 of aqueous humor.
7. Injected 0.1 cc of viscoelastic material (collvisc) through the same penetration site.
8. Applied 1% Cyclopentolate Hydrochloride (Cyclogyl, Alcon, U.S.A.).

In 9 New Zeland White rabbits (9 experimental, 9 control-BSS eyes), the anterior chamber of an eye was evacuated and the chamber re-filled with collvisc as described above.

The nine experimental animals exhibited mild inflammation of the eyes which subsided in 24 hours. The experimentally tested eyes compared well with the control eyes and no increase in intraocular pressure was observed in any of the animals.

EXAMPLE 2

Rabbit surgery trials by an ophthalmologist were carried out with collvisc. Collvisc was used to maintain the A.C. in a typical A.C. intraocular lens implantation performed according to the following protocol:

IOL Implantations with ECLE-Rabbit A.C. IOL Implantation using Collvisc

1. General anesthesia induced by Ketaset 20 mg/kg and rompun 15 mg/kg given I.M.
2. SLE exam of the anterior segment.
3. Pentobarbitol 65 mg/g through an I.V.E.Z. set, with 27 g needle given as needed via the marginal ear vein.
4. Cyclogyl 1% and Neo-synephrine 2½% eye drops given several times to dilate the pupil, thus facilitating removal of the lens.
5. Insert a wire speculum.
6. Hemostasis and bleeder vessels cautery.
7. Penetration into the A.C. through a small cornea-scleral incision at the superior limbus.
8. Place 0.1 cc heparin into the A.C.
9. Use the irrigating cystotome to perform an anterior capsulotomy.
10. Extend the incision.
11. Pull out the anterior capsule and clip off.
12. Express the nucleus.
13. Place temporary sutures and use the I/A machine to extract the cortex.
14. Remove temporary sutures.
15. Inject collvisc into A.C. to maintain chamber.
16. Inject Miochol (Acetylcholine 1:100, Coopervision, U.S.A.) into the A.C. to constrict the pupil.
17. Slip the IOL into the A.C. and fit the haptics in the angle.
18. Center the lens.
19. Place saline into the A.C. and irrigate to flush collvisc.
20. Close the wound with 10-0 Nylon Sutures.
21. Apply maxitrol ointment (Neomycin 3.5 mg/g+Polymyxin B 10,000 m/g and dexamethasone 0.1% Alcon, U.S.A.) and cyclogyl eye drops (cyclopentalate 1%, Alcon, U.S.A.). In case a more effective mydriasis is needed, apply Neo-synephrine 2½% (Phenylephrine 2½% Winthrop, U.S.A.) or Atropine 1%.

Post-Operative Follow-up

Each rabbit was examined regularly by SLE (slit lamp examination) post-op. No significant intraocular pressure rise was noted and after normal post-op inflammation, eyes became normal and quiet (within a few days).

Collvisc performed adequately in handling, maintaining the anterior chamber and irrigation from the anterior chamber.

I claim:
1. An opthalmic surgical procedure comprising;
    forming a viscoelastic solution by mixing purified collagen type II having a molecular weight of 285,000 with purified collagen type IV having a molecular weight of 532,000;
    placing said solution into an injection means;
    injecting said solution into the anterior chamber of a human eye.

* * * * *